US010059979B2

(12) United States Patent
Oster et al.

(10) Patent No.: US 10,059,979 B2
(45) Date of Patent: Aug. 28, 2018

(54) SPHERICAL, MAGNETIZABLE POLYVINYL ALCOHOL MICROPARTICLES, METHODS FOR THEIR PRODUCTION, AND THEIR USE

(71) Applicant: PerkinElmer Chemagen Technologie GmbH, Baesweiler (DE)

(72) Inventors: Jürgen Oster, Herzogenrath (DE); Thomas Sommer, Erkelenz (DE); Lothar À Brassard, Heinsberg (DE)

(73) Assignee: PerkinElmer chemagen Technologie GmbH, Baesweiler (DE)

( * ) Notice: Subject to any disclaimer, the term of this patent is extended or adjusted under 35 U.S.C. 154(b) by 615 days.

(21) Appl. No.: 14/416,219

(22) PCT Filed: Jul. 18, 2013

(86) PCT No.: PCT/EP2013/002145
§ 371 (c)(1),
(2) Date: Jan. 21, 2015

(87) PCT Pub. No.: WO2014/015966
PCT Pub. Date: Jan. 30, 2014

(65) Prior Publication Data
US 2015/0203895 A1  Jul. 23, 2015

(30) Foreign Application Priority Data

Jul. 21, 2012 (DE) .................. 10 2012 014 536

(51) Int. Cl.
| | |
|---|---|
| *C12Q 1/6806* | (2018.01) |
| *B03C 1/01* | (2006.01) |
| *C08J 3/14* | (2006.01) |
| *G01N 33/543* | (2006.01) |
| *H01F 1/44* | (2006.01) |
| *C08J 3/21* | (2006.01) |
| *C08J 3/24* | (2006.01) |
| *H01F 1/01* | (2006.01) |

(52) U.S. Cl.
CPC .............. *C12Q 1/6806* (2013.01); *B03C 1/01* (2013.01); *C08J 3/14* (2013.01); *C08J 3/21* (2013.01); *C08J 3/24* (2013.01); *G01N 33/5434* (2013.01); *G01N 33/54346* (2013.01); *H01F 1/01* (2013.01); *H01F 1/445* (2013.01); *C08J 2329/04* (2013.01)

(58) Field of Classification Search
CPC ... C12Q 1/6806; B03C 1/01; G01N 33/54326
USPC ........................................................ 435/6.1
See application file for complete search history.

(56) References Cited

U.S. PATENT DOCUMENTS

| | | | |
|---|---|---|---|
| 6,204,033 B1 | 3/2001 | Muller-Schulte | |
| 6,958,372 B2 | 10/2005 | Parker et al. | |
| 2001/0014468 A1* | 8/2001 | Muller-Schulte | ......... B03C 1/01 |
| | | | 435/181 |
| 2003/0109618 A1 | 6/2003 | Parker et al. | |

FOREIGN PATENT DOCUMENTS

| | | |
|---|---|---|
| DE | 10013995 A1 | 9/2001 |
| DE | 10103652 A1 | 8/2002 |
| DE | 10205332 A1 | 8/2003 |
| DE | 102008015365 A1 | 9/2009 |
| EP | 1118676 A2 | 7/2001 |
| WO | 9704862 A1 | 2/1997 |
| WO | 0170831 A1 | 9/2001 |
| WO | 2009115176 A2 | 9/2009 |
| WO | 2010149150 A2 | 12/2010 |

OTHER PUBLICATIONS

Int'l Search Report dated Jan. 23, 2014 in Int'l Application No. PCT/EP2013/002145.
Int'l Preliminary Examination Report dated Oct. 24, 2014 in Int'l Application No. PCT/EP2013/002145.
Written Opinion dated Jan. 23, 2014 in Int'l Application No. PCT/EP2013/002145.
Written Opinion dated Jul. 25, 2014 in Int'l Application No. PCT/EP2013/002145.
Müller-Schulte, et al, "Novel magnetic microspheres on the basis of poly(vinyl alcohol) as affinity medium for quantitative detection of glycated haemoglobin," Journal of Chromatography A, vol. 711, pp. 53-60 (1995).
Yang et al, "Preparation and Characterization of Monodisperse Superparamagnetic Poly(vinyl alcohol) Beads by Reverse Spray Suspension Crosslinking," Journal of Polymer Science Part A: Polymer Chemistry, vol. 46, No. 1, pp. 203-210 (2007).
PerkinElmer Chemagen, "M-PVA Magnetic Beads" (Apr. 14, 2012).
Oster et al, "Polyvinyl-alcohol-based magnetic beads for rapid and efficient separation of specific or unspecific nucleic acid sequences," Journal of Magnetism and Magnetic Materials, vol. 225, pp. 145-150 (2001).

(Continued)

*Primary Examiner* — Jezia Riley
(74) *Attorney, Agent, or Firm* — Panitch Schwarze Belisario & Nadel LLP

(57) ABSTRACT

Spherical, magnetizable polyvinyl alcohol microparticles, methods for their production, and use thereof are provided in the invention. The microparticles are especially useful for diagnostic purposes. The method enables the production of microparticles having a particle size distribution in the range of 0.5 to 3 µm, and includes the following steps, dispersing a nanoparticulate, magnetizable material in an aqueous phase which contains polyvinyl alcohol in dissolved form, adding the aqueous phase to an organic phase, immiscible with said aqueous phase and containing at least one emulsifier, producing an emulsion by stirring at a temperature of 25° C. or higher, and adding at least one water-soluble crosslinking agent while stirring is continued.

27 Claims, No Drawings

(56) References Cited

OTHER PUBLICATIONS

Response to Office Action dated Feb. 27, 2014 in Int'l Application No. PCT/EP2013/002145.
Response to Office Action dated Sep. 5, 2014 in Int'l Application No. PCT/EP2013/002145.
Sipos, "Manufacturing of size controlled magnetite nanoparticles potentially suitable for the preparation of aqueous magnetic fluids," Romanian Reports in Physics, vol. 58, No. 3, pp. 269-272 (2006).
Ye et al, "Room Temperature Solvent-Free Synthesis of Monodisperse Magnetite Nanocrystals," Journal of Nanoscience and Nanotechnology, vol. 6, pp. 852-856 (2006).

* cited by examiner

SPHERICAL, MAGNETIZABLE POLYVINYL ALCOHOL MICROPARTICLES, METHODS FOR THEIR PRODUCTION, AND THEIR USE

CROSS-REFERENCE TO RELATED APPLICATIONS

This application is a Section 371 of International Application No. PCT/EP2013/002145, filed Jul. 18, 2013, which was published in the German language on Jan. 30, 2014, under International Publication No. WO 2014/015966 A3 and the disclosure of which is incorporated herein by reference.

BACKGROUND OF THE INVENTION

The invention relates to spherical, magnetizable polyvinyl alcohol microparticles which are suited in particular for use in diagnostic detection methods or for isolation and purification of biomolecules. The invention further relates to methods of production by means of which the said microparticles can be produced on a larger scale.

Magnetic particles of the above-mentioned type are being used in a large number of diagnostic methods or in biomedical or biomolecular research. Generally, they are spherical particles which contain a superparamagnetic material in colloidal form, said material being embedded in a polymer matrix or enveloped in a polymer shell. Typically, these magnetic particles are microparticles of a size in the range of 1 to 20 µm.

Due to their ability to bind target substances such as biomolecules or cells selectively and, as the case may be, reversibly, magnetizable microparticles are particularly suitable for use in automated processes. As the magnetizable microparticles can be temporarily immobilized by applying a magnetic field, separation from liquid media does not require any centrifugation steps. This facilitates automation even in multi-stage processes, and it leads to considerable savings in time.

Magnetizable polymer-based microparticles, their preparation and their use have already been described in the prior art, for example in WO 97/04862 A1 and in the printed publications cited therein.

WO 97/04862 A1 discloses bead-shaped or spherical particles of polyvinyl alcohol which are described therein as being suitable for the fractionation of cells, nucleic acids, proteins, viruses or bacteria, as well as for use in immunoassays, for DNA sequencing or DNA synthesis.

The particles described in WO 97/04862 A1 comprise a polymer matrix of polyvinyl alcohol which has magnetic colloids of particle sizes of 10-200 nm encapsulated therein. The bead-shaped or spherical polymer particles have a particle size in the range of 1-10 µm, preferably 1-4 µm.

The production of the magnetizable polymer particles described in WO 97/04862 A1 is executed in such a manner that an aqueous polyvinyl alcohol solution in which a magnetic colloid is dispersed is suspended at room temperature, by stirring, in an organic phase (e.g. vegetable oil) immiscible with the polymer phase and containing at least two emulsifying agents. During this suspension process, the polyvinyl alcohol is crosslinked by addition of a water-soluble crosslinking agent reacting with hydroxyl groups, for example glutaraldehyde. The polyvinyl alcohol particles can subsequently be modified for the specific binding of biomolecules, for example by grafting on of spacer molecules which can serve to bind biomolecules.

It has, however, turned out that methods of production described in WO 97/04862A1 and the particles obtainable thereby are disadvantageous in various respects.

First of all, it is problematic that the magnetizable polymer particles prepared in accordance with that known method have a too wide particle size distribution and that the particle size distribution can vary from one batch to another, that is, batch reproducibility is dissatisfactory. When using the particles in separation processes, these varying values lead to non-uniform yields so that in many applications these particles cannot be used.

In addition, the magnetizable polymer particles prepared in accordance with the method described in WO 97/04862 A1 contain high proportions of particles having a size of less than 0.5 µm and having a size of more than 3 µm.

Particles of a size of less than 0.5 µm do not have sufficient separation velocity, or mobility, in an external magnetic field, so that given the commonly used magnetic field strengths, they are separated only very slowly, which adversely affects the total processing time. In addition, there is a risk of these particles, which can be separated only slowly or not at all, to be carried over as impurities and impede and falsify subsequent reactions or measurements, e.g. UV measurements or polymerase chain reactions (PCR).

Particles of a size of more than 3 µm have the disadvantage of sedimenting relatively quickly in the gravitational field, which markedly limits their capacity of binding biomolecules. Hence, it can become necessary to counteract sedimentation by appropriate measures (re-dispersion). In addition, the greater the particle size of the magnetizable polymer particles, the smaller the total surface area, relative to the total mass or the suspension volume. This in turn leads to a lower yield in substances to be separated (biomolecules, cells). All in all, both the presence of particles that are too small (<0.5 µm) and the presence of particles that are too large (>3 µm) render the process of magnetic separation more difficult, for example in automated nucleic acid purification.

Furthermore, the magnetizable polyvinyl alcohol particles produced with the methods described in WO 97/04862 A1 contain only a relatively low content of magnetizable material (magnetite/iron oxide), namely in the range of about 7 to 24 percent by weight. This leads to insufficient or unfavorable separation properties of the particles in the magnetic field.

Owing to the above-described disadvantages in terms of particle sizes, particle size distribution and magnetite content, the usability of the magnetizable polymer particles prepared in accordance with the method described in WO 97/04862 A1 is limited. The magnetizable polymer particles are poorly suited, in particular, for use in automated separation methods and analytical methods.

It has turned out to be particularly disadvantageous that when used in PCR methods the magnetizable polymer particles known in the state of the art have an inhibitory effect, whereby the detection sensitivity is reduced and the accuracy and, thereby, reliability of the measurements are adversely affected. Since PCR techniques are widely used in molecular biology research and medical diagnostics, and the use of magnetizable microparticles is gaining in importance with regard to the automation of these methods, the above mentioned inhibiting effect of the particles known in the state of the art is highly dissatisfactory.

It has furthermore turned out that the methods of production described in WO 97/04862 A1 are not suitable for the production of magnetizable polyvinyl alcohol particles on a larger scale. With these known methods, the volume of the reaction batch is limited to a maximum of around 5 L, and the yield of magnetizable polymer particles is too low. Hence, it is not possible with these known production methods to cost-effectively produce magnetizable polyvinyl alcohol particles in larger quantities and with the required quality characteristics (particularly if the particle size distribution is narrow).

BRIEF SUMMARY OF THE INVENTION

In view of the above-mentioned disadvantages and requirements, the object of the invention is to provide magnetizable polyvinyl alcohol particles of the kind mentioned hereinabove, which are characterized by a narrow particle size distribution in the range of 0.5-3 µm. In the intended applications, especially when used in automated methods of application, they enable high processing speeds (i.e. high throughput), improved efficiency in separating the target substances (especially with regard to the purity of the product) and/or increased yields. In PCR applications they have no inhibiting effect or only a minor inhibiting effect.

Another object of the invention is to provide methods of production by means of which it is possible to produce the magnetizable microparticles according to the invention and, in particular, to produce them in a batch-consistent manner. It is a further object of the invention to provide methods of production by means of which it is possible to produce the magnetizable microparticles on a larger scale, and at the above-mentioned narrow particle size distribution. Specifically, in quantities of 200 g or more, preferably 500 g or more, more preferably 1 kg or more, in each case per reaction batch.

The aforementioned objects are solved by the production methods and spherical, magnetizable polyvinyl alcohol microparticles as claimed in the independent patent claims, as well as by the special or preferred embodiments defined in the dependent claims, and by the further embodiments which will become apparent from the following description. With the inventive method features, particularly in their entirety, it is possible to obtain spherical, magnetizable polyvinyl alcohol microparticles having the improved particle properties mentioned, as will be explained in the following.

The method according to the invention, which makes possible the production of spherical, magnetizable polyvinyl alcohol microparticles having a narrow particle size distribution in the range of 0.5 to 3 µm and/or having further, aforementioned advantageous properties on the production scale (e.g. 200 g per batch, or more), comprises at least the following steps:

(1) dispersing a nanoparticulate, magnetizable material, preferably magnetite, in an aqueous phase which contains polyvinyl alcohol (PVA) in dissolved form (aqueous polyvinyl alcohol solution);

(2) adding the aqueous phase to an organic phase, which is immiscible with said aqueous phase and contains at least one emulsifier, and producing an emulsion by stirring at a temperature of 25° C. or higher;

(3) adding at least one water-soluble crosslinking agent suitable for crosslinking polyvinyl alcohol, while stirring is continued.

Without wanting to be committed to a particular theory, it is presumed that the formation of the spherical, magnetizable polyvinyl alcohol particles takes place in such a way that during the dispersion process (step (1)) thin PVA layers form on the individual particles of the nanoparticulate magnetizable material (e.g. magnetite), preventing the formation of particle agglomerates. In the emulsion produced according to step (2), the aqueous phase, which contains PVA and the magnetizable nanoparticles coated with PVA, together with the organic phase and the emulsifier forms an emulsion with spherical micelles. By crosslinking (step (3)), the nanoparticles are stabilized through covalent linkage of many PVA chains on the particle surface.

Owing in particular to the higher emulsifying temperature (step (2), 25° C. or higher), the formation of particles having a too low particle size (particularly <0.5 µm) is suppressed and the size maximum is shifted towards larger particles. The particles resulting therefrom show an optimal ratio of magnetizability (and separability) to surface capacity and sedimentation behavior. Furthermore, using the methods according to the invention a more efficient encapsulation of the magnetizable nanoparticulate material in the polyvinyl alcohol layer is achieved. This results in the above mentioned reduction, or lack of, inhibitory effects.

Due to the above-described method of production, the particles obtainable with the methods according the invention are essentially spherical, that is, ball-shaped or bead-shaped, as visible on the optical microscope.

DETAILED DESCRIPTION OF THE INVENTION

The term "magnetizable" means that the particles can be magnetized such that when exposed to an external magnetic field, they are magnetically attracted and can be separated from, for example, a liquid medium. When the magnetic field is switched off, the magnetization of the particles is cancelled, that is, the particles should preferably have a remanence of almost zero, or of zero.

The term "polyvinyl alcohol microparticles" means that the magnetizable microparticles, according to the invention, comprise a content of polyvinyl alcohol. This polymer, possibly in combination with further substances, forms a matrix in which the nanoparticulate magnetizable material is embedded or enclosed. According to a preferred embodiment, the polymer matrix of the magnetizable microparticles consists exclusively of polyvinyl alcohol.

The magnetizable polyvinyl alcohol microparticles obtainable with the inventive method have a narrow particle size distribution in the range of 0.5 to 3 µm, preferably in the range of 0.5 to 1 µm. According to another preferred embodiment, the polyvinyl alcohol microparticles have a particle size distribution in the range of 1.25 to 2.25 µm.

The term "narrow particle size distribution" refers, in particular, to the fact that at least 75%, preferably at least 90%, especially preferably at least 95% of the particles, have a particle size within the indicated size range of 0.5 to 3 µm, or 0.5 to 1 µm.

The particle size distribution is preferably monomodal, that is, within the range of 0.5 to 3 µm, or within the range of 0.5 to 1 µm, respectively, it has a single maximum.

In particular, ferromagnetic or super paramagnetic colloid particles can be used as the nanoparticulate magnetizable material to be dispersed in the aqueous polyvinyl alcohol solution, with nanocrystalline magnetite being particularly preferred.

Preferably, the nanoparticulate magnetizable material has a particle size in the range of 5 to 250 nm, particularly 5 to 100 nm and especially preferably 5 to 50 nm.

According to a preferred embodiment of the invention, the magnetizable nanoparticulate material used, preferably magnetite nanoparticles, is produced or pretreated by a method which is characterized by the following features:

suspending of magnetizable nanoparticles in deionized water having a conductance of less than 500 µS/cm, preferably less than 100 µS/cm, more preferably less than 5 µS/cm; treating the aqueous nanoparticle suspension by means of an ultrasonic homogenizer.

The initially used magnetizable nanoparticles can be produced with known methods (see, for example, Sipos P.: "Manufacturing of Size Controlled Magnetite Nanoparticles Potentially Suitable for the Preparation of Aqueous Magnetic Fluids"; Romanian reports in physics 2006; 58(3): 229-233.; and: YE X R et al.: "Room temperature solvent-free synthesis of monodisperse magnetite nanocrystals", J. Nanosci. Nanotechnol. 2006, Vol. 6, No. 3, pp. 852-856).

Preferably, the manufacture of the nanoparticles, as well as the further processing thereof, takes place without addition of surface-active substances.

By subjecting the nanoparticle suspension to the above-mentioned ultrasound treatment, it is possible to achieve an extensive destruction of any particle aggregates that might be present. The ultrasound treatment is preferably performed using the flow method.

The ultrasonic power is preferably at least 1000 W. The duration of the exposure to ultrasound is preferably at least 10 min, more preferably at least 0.5 h, and most preferably at least 1 h.

Suitable ultrasonic homogenizers for carrying out the above-mentioned ultrasonic treatment are known to those skilled in the art and commercially available (e.g. Dr. Hielscher Sonopuls 2000 W; Hielscher Ultrasonics GmbH, D-14513 Teltow).

It has furthermore turned out to be advantageous to subject the nanoparticle suspension to a centrifugation step prior to the further processing thereof, by means of which particles of a size of >250 nm, preferably of a size of >100 nm, are removed. Centrifugation is preferably performed at 1000-3000×g.

It was found that the magnetizable nanoparticles pretreated with the above-described methods are particularly suited for the production of the inventive magnetizable polyvinyl alcohol microparticles possessing the above-described advantageous properties (especially a narrow particle size distribution in the size range as indicated).

By using nanoparticulate magnetizable material, particularly magnetite, with grain sizes not exceeding 250 nm, preferably not exceeding 100 nm, it is possible to manufacture spherical, magnetizable polyvinyl alcohol microparticles containing a relatively high proportion of magnetizable material, especially magnetite.

Preferably, this proportion amounts to at least 50 percent by weight. According to a particularly preferred embodiment, the inventive particles have a magnetite content of 50 to 60 percent by weight (mean value: approx. 55%-wt).

The polyvinyl alcohol used for the preparation of the aqueous phase is preferably a polyvinyl alcohol having an average molar mass in the range of 50,000 up to 300,000 and a degree of hydrolysis in the range from 70 to 99.9 mole percent, preferably 80 to 95 mole percent. For example, the polyvinyl alcohol types available under the designation "Mowiol" are suitable for this purpose (Kuraray Europe GmbH, Frankfurt a. M.).

The concentration of polyvinyl alcohol in the aqueous phase preferably does not exceed 2 percent by weight and is more preferably 0.1 to 2 percent by weight and most preferably 0.5 to 1.5 percent by weight.

It has turned out that limiting the polyvinyl alcohol concentration in the aqueous phase to a maximum of 2.0 percent by weight, especially 1.5 percent by weight, contributes considerably to preventing the formation of particles with a diameter that is too large (in particular a diameter of more than 3 µm), and which owing to their sedimentation properties, would have an adverse effect on the later use of the particles, especially in the case of automated nucleic acid purification. Furthermore, the limitation of the polyvinyl alcohol concentration to a maximum of 2.0, preferably to 1.5 percent by weight, contributes to being able to obtain magnetizable polymer particles containing a high proportion of magnetizable material (e.g. magnetite), preferably containing a proportion of 50 percent by weight or more, and more preferably 50 to 60 percent by weight.

The magnetizable material, preferably magnetite, is preferably added to the aqueous phase in a proportion of 0.5 to 7.5 percent by weight, more preferably of 1 to 5 percent by weight.

The dispersing process in the first step of the method can be performed by means of known methods, usually employing a dispersing apparatus (e.g. dispersing apparatus ULTRA-TURRAX®) or a propeller mixer. If required, the dispersion process can be carried out while heating in order to ensure that the polyvinyl alcohol is dissolved as completely as possible.

In a preferred embodiment of the method, the aqueous phase containing polyvinyl alcohol and magnetizable material is homogenized by means of an ultrasonic homogenizer prior to adding to the organic phase. In this way the magnetizable material can, if desired or necessary, be reduced to a particle size of less than 250 nm, preferably less than 100 nm (hydrodynamic diameter). This additional homogenizing step furthermore has the advantage that any possibly present particle aggregates or agglomerates are reduced in size. Suitable ultrasonic homogenizers are known to those skilled in the art and are commercially available (e.g. "Labsonic™ P", Sartorius A G, Göttingen; "Dr. Hielscher Sonopuls 2000 W").

Addition of emulsifiers to the aqueous polymer phase is not necessary, due to the special features of the methods of production, according to the invention.

In a second or further step of the method of production according to the invention, the aqueous phase is added to an organic phase, which is immiscible with said aqueous phase, and contains at least one emulsifier. Then, an emulsion is produced while stirring at a temperature of 25° C. or higher. The temperature is preferably 30° C., 40° C. or higher, more preferably at least 50° C., in particular 55 to 65° C., and most preferably 60° C. Surprisingly, it has turned out that the formation of very small particles (less than 0.5 µm) can be reduced or prevented if the production of the particles is performed at an elevated temperature, as indicated, with the elevated temperatures indicated above (≥30° C., ≥40° C., ≥50° C., ≥60° C.) having a particularly favorable effect.

Depending on the type of the dispersing or stirring apparatus used, the volume of the emulsion, etc., the emulsion process is generally completed after 10 s to 15 min.

The emulsion can be produced, in a manner known to the skilled artisan, using a common dispersing or stirring apparatus, for example at stirring speeds in the range of 500 to 5000 rpm.

For producing the emulsion, in accordance with the invention, it has proved to be particularly advantageous to use a dispersion mixer operating according to the rotor-stator principle. The rotor speed used is typically in the range of 500 to 4000 rpm. Conventionally, the mixing head of the dispersion mixer is immersed in the liquid to be emulsified, which is contained in a closed container. The volume capacity of the container can be up to 100 L, for example 10 to 100 L, or several 100 L, for example 100 to 500 L.

The dispersing or emulsifying process is performed, using the above-mentioned dispersion mixer, essentially without introduction of air. Preferably, the dispersion mixer is equipped with a mixing head, the stator of which (surrounding the rotor) is provided with a plurality of vertical slots. During rotation, a vertical, downward flow of liquid, as well as a horizontal flow of liquid are formed. The latter causes the liquid to be emulsified to pass through the slots of the mixing head, which, due to the high shearing forces occurring in the process and to the turbulences formed in the mixing head, leads to a very efficient, thorough mixing and homogenization. This, in particular, facilitates a rapid distribution of the crosslinking agent in the suspension.

Dispersion mixers of the aforementioned type are known to those skilled in the art; for example, a dispersion mixer from Ystral GmbH may be used ("Ystral Dispermix", Ystral GmbH, D-79282 Ballrechten-Dottingen).

When a dispersion mixer is used as described above, a particularly efficient deagglomeration and suspension is achieved. In addition, because of the high circulation performance of the dispersion mixer, it is possible to prevent localized overheating, and a quick distribution of the crosslinking agent can be attained. Unwanted "coalescence" of micelles is thereby suppressed or prevented. That is, formation of "multiple beads" or combinations of two or more micelles is impeded.

It was found that the use of a dispersion mixer of the aforementioned type is particularly advantageous if large emulsion volumes (10 L or more) are to be processed, with the batch consistency being maintained as constant as possible.

The above-described dispersing method is not only particularly advantageous with respect to the processing of larger batch volumes, but also with respect to increasing the yield in magnetizable polyvinyl alcohol microparticles. For example, given a batch volume (emulsion volume) of 100 L the yield in magnetizable, spherical polyvinyl alcohol particles is at least 200 g.

In particular, the following liquids are suitable for use as the water-immiscible organic phase: vegetable oils (e.g. rape oil or sunflower oil), mineral oils, synthetic oils, silicone oils and paraffin oils, as well as mixtures of the aforementioned oils.

Generally an excess volume, relative to the aqueous phase, of the organic, water-immiscible phase is used. The volume fraction of the organic water-immiscible phase preferably equals 3 to 50 times, particularly 3 to 25 times, more preferably 3 to 15 times, the volume of the aqueous phase.

The emulsifier used in the preparation of the emulsion is preferably selected from the following group of emulsifiers: propylene oxide-ethylene oxide block copolymers (poloxamers, e.g. Synperonic®, Tetronic®, Pluronic®), polysorbates (compounds that are formed by etherifying sorbitan fatty acid esters with polyethylene glycol; e.g. Tween®, preferably Tween® 80), sorbitan fatty acid esters (e.g. sorbitan laurate, sorbitan stearate, sorbitan oleate, sorbitan sesquioleate; e.g. Arlacel®, Span®, Dehymuls®), polyethoxylated fatty acids (ethoxylated fatty acid esters, fatty acid ethanolamides, alkylamine ethoxylate; e.g. lau-ryl, oleyl or stearylamine-PEG ether, triethanolamine-PEG ether), addition products of ethylene oxide or/and propylene oxide to fatty alcohols having 8 to 18 C atoms (e.g. Brij®, Eumulgin®, Polidocanol), polyoxyethylated hydrogenated castor oil (e.g. DEHYMULS® HRE 7), block copolymers of castor oil derivatives, polyoxyethylene-polyoxypropylene-ethylenediamine block copolymers, polyoxyethylene block copolymers of a polyhydroxy fatty acid and polyethylene oxide (e.g. Hypermer® A70), alkyl phenol ethoxylate (especially octyl phenol or nonyl phenol with 2-100 ethylene oxide units; e.g. Triton®, Triton® X-100), alkyl phenol prop-oxylates, pentaerythritol-fatty acid esters (e.g. penta-ery-thrityl mono-lau-rate), mixed esters of pentaerythritol-fatty acid esters and citric acid-fatty alcohol esters (e.g. Dehymuls® FCE), polyethylene glycols, alkyl benzene sulfonic acids and alkyl benzene sulfonates, partial esters of polyglycerin, sugar alcohols or alkyl glycosides with saturated and/or unsaturated, linear or branched fatty acids with 8 to 22 carbon atoms, polyhydroxy fatty acids-polyethylene glycol block copolymers, and phosphoglycerides such as phosphatidylcholine or phosphatidylethanolamine. Furthermore, mixtures or combinations of two or more emulsifiers may be used.

A preferred mixture of emulsifiers contains the following main constituents: (1) Tween® 80 (polyoxyethylene(20)-sor-bi-tan monooleate) and/or (2) Arlacel® 83 (sorbitan sesquioleate); (3) DEHYMULS® HRE 7 (ethoxylated (PEG-7), hydrogenated castor oil) and (4) Hypermer® A70 (polyoxyethylene block copolymers of a polyhydroxy fatty acid and polyethylene oxide).

Preferred mixtures of emulsifiers are those containing at least one lipophilic emulsifier in combination with at least one hydrophilic or amphiphilic emulsifier. Lipophilic emulsifiers are, in general, non-ionic tensides with an HLB value in the range of 3 to 8. These are also called W/O emulsifiers. Hydrophilic or amphiphilic emulsifiers typically have HLB values in the range of 8 to 18 and are also called O/W emulsifiers.

The group of lipophilic emulsifiers includes, for example: sorbitan-fatty acid esters (e.g. Span® 40), lecithin, PEG-PPG-PEG block copolymers (e.g. Pluronic® L31, L61, L81), PEG oleyl ethers (z. B. Brij® 93).

The group of hydrophilic or amphiphilic emulsifiers includes, for example: PEG-PPG-PEG block copolymers (e.g. Pluronic® L-64, Pluronic® 10R5), PEG-hexadecyl ether (e.g. Brij® C10), PEG octadecyl ether (z. B. Brij® S10), polyoxyethylene-nonylphenyl ether, polyoxyethylene-tridecyl ether, polyoxyethylene-sorbitan monostearate (e.g. Tween® 60), polyoxyethylene-sorbitan monolaurate (e.g. Tween® 20), polyoxyethylene stearyl ether (e.g. Brij® S100), poly-ethoxylated hydrogenated castor oil.

The emulsifier or the mixture of two or more emulsifiers can be added to, or dissolved in, the water-immiscible phase (oil phase), before the said phase is combined with the aqueous phase for emulsification.

The proportion of the emulsifier or the emulsifiers is preferably 0.1 to 10 percent by weight, more preferably 1 to 7.5 percent by weight, in each case relative to the organic phase.

During the emulsifying step or subsequent to that step, at least one water-soluble crosslinking agent suitable for the crosslinking of polyvinyl alcohol is added, whereby the spherical polyvinyl alcohol particles are stabilized by covalent crosslinking.

The addition of crosslinking agent(s) preferably takes place during the emulsifying process, which means that the two phases are initially dispersed or emulsified without the presence of the crosslinking agent, by stirring, whereupon the crosslinking agent is added and the stirring process is continued until the crosslinking reaction is completed (generally about 10 s to 5 min following addition of the crosslinking agent). Preferably, the crosslinking step is likewise performed at an elevated temperature, as indicated hereinabove regarding the emulsifying step. The elevated temperature (>25° C.) used in the emulsifying step can be maintained during the crosslinking reaction as well.

Preferably, bifunctional aldehydes, especially glutar-aldehyde, as well as acid chlorides or divinyl sulfone are used, with glutaraldehyde being particularly preferred. By contrast, the use of diamines as crosslinking agents (e.g. hexamethylenediamine) has proved unfavorable since the free amino groups are able to enter into unwanted side reactions with biomolecules.

The emulsifiers are usually added to the emulsion in liquid form, i.e. as solutions (e.g. aqueous solutions), the said solutions containing the crosslinking agent(s) preferably at a total concentration of 1 to 40 percent by weight, preferably 5 to 25 percent by weight. According to a preferred embodiment, a 12.5% aqueous glutaraldehyde solution is used.

The proportion of the crosslinking agent(s) added to the emulsion is preferably 0.1 to 10 percent by volume, particularly 1 to 7.5 percent by volume, in each case relative to the aqueous phase.

Furthermore, the crosslinking step is performed using bifunctional aldehydes, especially glutaraldehyde, preferably with addition of acid, because in this way the crosslinking reaction can be considerably accelerated. According to the invention, it has surprisingly been found that acid addition of 10 percent by volume or less, preferably 5 percent by volume or less, more preferably 3.2 percent by volume or less, in each case relative to the aqueous polymer phase, is sufficient to accelerate the crosslinking caused by glutaraldehyde, and to prevent any aggregate formation of the nanoparticulate magnetizable material. The volume percentages relate to 1N to 3N HCl.

Addition of acid preferably takes place before the emulsifying step, that is, the acid is added to the aqueous phase. Alternatively, the acid can be added during emulsification or after emulsification is completed.

Apart from HCl, the following acids are suitable as acids to be added: a) nitric acid 1-3 N (acid addition to the polymer phase at a maximum of 10 percent by volume), b) sulphuric acid 1-3 N (acid addition to the polymer phase at a maximum of 5 percent by volume), c) HBr, d) acetic acid, and e) phosphoric acid.

Furthermore, it has been found that higher acid concentrations (i.e. more than 10 percent by volume)—especially at higher temperatures (>60° C.)—lead to a decomposition of the nanoparticulate magnetizable material, particularly of the magnetite, and thereby lead to an unwanted release of iron ions. Thus, the inventive reduction of the acid added during the crosslinking step can contribute to obtaining magnetizable polyvinyl alcohol particles which contain a high proportion of magnetizable material, preferably magnetite, namely at least 50 percent by weight, or up to 90 percent by weight.

Usually, the crosslinking reaction is completed within about 10 s to 5 min following addition of the crosslinking agent or agents. Subsequently, the spherical magnetizable polyvinyl alcohol microparticles can be separated from the liquid reaction mixture by known methods (e.g. by centrifugation or magnetic separation). To separate any impurities (e.g. oil, emulsifiers) that may adhere to the particles, the microparticles may be washed using suitable solvents or solvent mixtures (e.g. water, ethanol, methanol, 2-propanol, n-hexane, acetone, methyl ethyl ketone), in each case by re-suspending and centrifugation or magnetic separation of the particles.

In a preferred embodiment, the inventive method comprises at least the following steps:
  dispersing a nanoparticulate magnetizable material, preferably magnetite, in an aqueous phase containing polyvinyl alcohol in dissolved form, with the concentration of polyvinyl alcohol in the aqueous phase not exceeding 2.0 percent by weight, and preferably amounting to 0.1 to 2.0 percent by weight, more preferably 0.5 to 1.5 percent by weight, and with the concentration of the magnetizable material, or of the magnetite, in the aqueous phase preferably being 0.5 to 7.5 percent by weight, more preferably 1 to 5 percent by weight;
  adding the aqueous phase to an organic phase which is immiscible with said aqueous phase and contains at least one emulsifier, and producing an emulsion by stirring at a temperature of at least 50° C., preferably at 55 to 65° C., more preferably 60° C.;
  adding at least one water-soluble crosslinking agent which is suitable for crosslinking polyvinyl alcohol, while stirring is continued.

In another preferred embodiment, the method according to the invention comprises at least the following steps:
  dispersing a nanoparticulate magnetizable material, preferably magnetite, which has a particle size not exceeding 250 nm, preferably not exceeding 100 nm, in an aqueous phase containing polyvinyl alcohol in dissolved form, with the concentration of polyvinyl alcohol in the aqueous phase not exceeding 2.0 percent by weight and preferably amounting to 0.1 to 2.0 percent by weight, more preferably 0.5 to 1.5 percent by weight, and with the concentration of the magnetizable material, or of the magnetite, in the aqueous phase preferably being 0.5 to 7.5 percent by weight, more preferably 1 to 5 percent by weight;
  adding the aqueous phase to an organic phase which is immiscible with said aqueous phase and contains at least one emulsifier, and producing an emulsion by stirring at a temperature of at least 25° C., preferably at 50 to 65° C., more preferably 60° C.;
  adding at least one bifunctional aldehyde as a crosslinking agent, with addition of hydrochloric acid (1N up to 3N) at a volume percent of up to 5%, relative to the aqueous phase.

In yet another preferred embodiment, the method according to the invention comprises at least the following steps:
  dispersing a nanoparticulate magnetizable material, preferably magnetite, in an aqueous phase containing polyvinyl alcohol in dissolved form, with the concentration of polyvinyl alcohol in the aqueous phase not exceeding 2.0 percent by weight and preferably amounting to 0.1 to 2.0 percent by weight, more preferably 0.5 to 1.5 percent by weight, and with the concentration of the magnetizable material, or of the magnetite, in the aqueous phase preferably being 0.5 to 7.5 percent by weight, more preferably 1 to 5 percent by weight;
  adding the aqueous phase to an organic phase which is immiscible with said aqueous phase and contains at least one emulsifier, and producing an emulsion by stirring at a temperature of 25° C. or higher, preferably at 50 to 65° C., more preferably at 60° C., said emulsion being produced using a dispersion mixer which operates according to the rotor-stator principle, at a rotor speed in the range of 500 to 4000 revolutions/min, and the volume of the emulsion being 10 L or more;

adding at least one water-soluble crosslinking agent which is suitable for crosslinking polyvinyl alcohol, while stirring is continued.

In a particularly preferred embodiment, the method according to the invention comprises at least the following steps:

dispersing a nanoparticulate magnetizable material, preferably magnetite, in an aqueous phase containing polyvinyl alcohol in dissolved form, with the concentration of polyvinyl alcohol in the aqueous phase not exceeding 2.0 percent by weight and preferably amounting to 0.1 to 2.0 percent by weight, more preferably 0.5 to 1.5 percent by weight, and with the concentration of the magnetizable material, or of the magnetite, in the aqueous phase preferably being 0.5 to 7.5 percent by weight, more preferably 1 to 5 percent by weight;

adding the aqueous phase to an organic phase which is immiscible with said aqueous phase and contains at least one emulsifier, and producing an emulsion by stirring at a temperature of at least 50° C., preferably at 55 to 65° C., more preferably at 60° C., said emulsion being produced by using a dispersion mixer which operates according to the rotor-stator principle, at a rotor speed in the range of 500 to 4000 revolutions/min, and the volume of the emulsion being 10 L or more;

adding at least one bifunctional aldehyde, preferably glutaraldehyde, as a crosslinking agent, with addition of hydrochloric acid (1N up to 3N) at a volume percent of up to 10%, preferably up to 5%, more preferably 3.2%, in each case relative to the aqueous phase.

Each of the afore-described embodiments can be combined with one or more of the features described further above.

According to a particularly preferred embodiment, the nanoparticulate magnetizable material, preferably magnetite, used in the first method step of the method of production according to the invention, is subjected to a treatment method comprising the following steps:

suspending magnetizable nanoparticles in deionized water having a conductance of less than 100 µS, preferably less than 5 µS/cm;

treating the aqueous nanoparticle suspension by means of an ultrasound homogenizer, preferably at an ultrasound power of at least 1000 W and a duration of sonication of at least 10 min, preferably at least 0.5 h. Ultrasonication is preferably conducted using the continuous method (flow method).

With the methods according to the invention it is possible to obtain spherical, magnetizable polyvinyl alcohol particles having a narrow particle size distribution in the range of 0.5-3 µm, for example in quantities of at least 200 g per batch. The size of a batch, that is, the volume of the emulsion used for production, can be 5 L or more, preferably 10 L or more, for example 50 to 150 L or several hundreds of liters (e.g. 200-500 L).

Optionally, the particle size may be influenced by altering one or several of the following parameters (taking into account the limits regarded as essential to the invention, as indicated in the above description):

polymer concentration (low concentration causes reduction in particle size);

stirring speed during emulsifying (higher speed causes reduction in particle size);

selection of the emulsifier(s) and emulsifier concentration.

The polyvinyl alcohol microparticles prepared with the methods according to the invention can, without further modification, be used to bind, for example, biomolecules, more particularly by binding to the free OH groups of the polyvinyl alcohol, or they may be activated or modified by various reactions known to the skilled artisan, in order to enable the binding of biomolecules, cells etc. Using the modification reactions mentioned, it is possible to couple, for example, functional groups or, for example, spacer molecules, to the particle matrix or particle surface.

Preferred examples of such known activation or modification reactions are described in WO 97/04862 A1 and in the printed publications cited therein. In this connection, activation by means of activation reagents, such as cyanogen bromide (for coupling of ligands with primary amino groups, e.g. antibodies), epichlorohydrin, 1,1'-carbonyldiimidazol or hexamethylene diisocyanate should be mentioned, in particular.

Spacer molecules can be introduced in a manner known per se by graft polymerisation of vinyl monomers (especially acrylic monomers) under the catalytic influence of Cer(IV) salts, as cited in WO 97/04862 A1 and in the printed publications cited therein.

The spacers coupled to the magnetizable polyvinyl alcohol microparticles can then be used, for example, for the binding of biomolecules.

The invention furthermore relates to spherical, magnetizable polyvinyl alcohol microparticles having a particle size distribution in the range of 0.5 to 3 µm, obtainable according to any one of the above-described methods of production according to the invention. Preferably, the microparticles have a size distribution in the range of from 0.8 to 3 µm or, more preferably, in the range of 0.5 to 1 µm. According to another, preferred embodiment, the microparticles have a size distribution in the range of 1.25 to 2.25 µm.

In the above connection, the indication of "size distribution in the range of . . . " means that at least 75%, preferably at least 90%, more preferably at least 95% of the particles have a particle size lying within the respective size range indicated.

The particle size distribution of the microparticles according to the invention can be described as being monomodal, that is, it essentially has only one single maximum.

The particle size can be determined in a manner known to the skilled artisan, for example by means of DLS/PCS (dynamic light scattering/photon correlation spectroscopy). Measuring apparatuses suited for this purpose are commercially available (e.g. Beckman Coulter, Inc. Delsa™ Nano C, D-47807 Krefeld).

The PCS method used yields as a result the average particle size of the sample measured and an associated polydispersity index (PDI), which is a measure for the width of the particle size distribution. In the case of the magnetizable microparticles produced with the methods according to the invention, which have a narrow size distribution, the polydispersity index (PDI) is preferably 0.25 or below, more preferably between 0.1 and 0.25.

According to a preferred embodiment, the inventive magnetizable microparticles are characterized by the fact that the content of nanoparticulate material, particularly of magnetite, is at least 50 percent by weight, preferably at least 60 percent by weight, more preferably at least 75 percent by weight, and particularly up to 90 percent by weight. This can be achieved, in particular, by limiting the polyvinyl alcohol concentration in the aqueous phase to a maximum of 1.5 percent by weight, as described above. Due to the increased magnetite content and because of their narrow particle size distribution (as indicated above) these magnetizable microparticles are characterized by exhibiting improved separation properties in the magnetic field.

The content of magnetizable inorganic material can be determined in a manner known to those skilled in the art, for example by combustion analysis.

Due to the high magnetite content of the magnetizable microparticles according to the invention, it is still possible to ensure good magnetic separation characteristics even at reduced particle size (e.g. in the range of 0.5 to 1 µm). Particularly preferred particles according to the invention are therefore those that have a particle size distribution in the range of 0.5 to 1 µm and a magnetite content of 50 to 90 percent by weight, preferably 50 to 75 percent by weight, more preferably 50 to 60 percent by weight.

Despite their increased magnetite content (at least 50 percent by weight, preferably 50 to 60 percent by weight, more preferably at least 60 percent by weight), the magnetizable microparticles prepared, or obtainable, with the methods according to the invention are characterized by a marked reduction in non-specific binding (especially of proteins) when they are used in the detection methods mentioned, in particular in PCR. This reduction in non-specific binding is due to the fact that with the methods of production according to the invention, a particularly efficient encapsulation of the magnetizable material (e.g. magnetite) is achieved. As a result, the proportion of free magnetite (or of nanoparticulate magnetizable material), which is responsible for non-specific bindings is extremely small.

The more efficient encapsulation of the magnetite, and thereby the reduction of the free magnetite proportion, can be proved by a measurable change in the zeta potential of the particles compared with conventional particles (e.g. WO 97/04862 A1) (see Example 3 and Table 1). The particles which are prepared, or obtainable, with the methods according to the invention preferably exhibit a zeta potential that is increased by at least 15%, preferably by 25%, particularly by 30% (relative to the absolute value of the zeta potential). It is assumed that the change in zeta potential observed is due to the reduction of the free magnetite present on the particle surface (while the particle size and particle surface area remain unchanged), and that the zeta potential can thus be regarded as a measure for the efficiency of the encapsulation of the magnetite. The zeta potential of the magnetic microparticles is preferably ≤−35 mV, more preferably ≤−40 mV.

The invention therefore comprises spherical, magnetizable polyvinyl alcohol microparticles with a content of nanoparticulate magnetizable material, the microparticles having a zeta potential of ≤−35 mV, more preferably ≤−40 mV.

The particle size distribution preferably lies in the range from 0.5 to 3 µm, and more preferably in the range from 0.5 to 1 µm or in the range from 1.25 to 2.25 µm.

The content of nanoparticulate magnetizable material, particularly of magnetite, is preferably at least 50 percent by weight, more preferably at least 60 percent by weight, most preferably at least 75 percent by weight. It is possible for the said content to amount to up to 90 percent by weight.

The magnetizable microparticles obtainable or prepared by the method according to the invention are furthermore characterized in that in PCR applications they have a markedly reduced inhibitory influence on the PCR reaction, or in that such an influence is entirely missing, compared with pre-known microparticles (see Example 4 and Tables 3 and 4). The presence of inhibitory components in the PCR reaction batch leads to a delay in the amplification reaction and thereby to an increase of the Ct value. In "real time quantitative PCR", that value indicates the number of cycles needed until the fluorescence signal exceeds the threshold and the exponential phase of the PCR begins. Since the Ct value is inversely proportional to the amount of the nucleic acids contained in the sample, the presence of inhibitory components (such as microparticles with inhibitory action) leads to a falsification of the results.

Surprisingly, it was found that when the magnetizable microparticles obtainable or prepared with the methods according to the invention are used in PCR applications, the Ct value remains unaltered or is increased by at most 2%, preferably at most 1%, more preferably at most 0.5%.

Hence, the invention comprises spherical, magnetizable polyvinyl alcohol microparticles having a content of nanoparticulate magnetizable material, wherein the microparticles, when used in PCR methods, do not cause a change in the Ct value or cause only a slight increase of the Ct value, preferably by at most 2%, more preferably by at most 1%, particularly by at most 0.5%.

The particle size distribution is preferably in the range of 0.5 to 3 µm, and more preferably in the range of 0.5 to 1 µm or in the range of 1.25 to 2.25 µm. The content of nanoparticulate magnetizable material, particularly of magnetite, is preferably at least 50 percent by weight, more preferably at least 60 percent by weight, most preferably at least 75 percent by weight. It is possible for the said content to amount to up to 90 percent by weight.

The magnetizable microparticles according to the invention have functional groups which enable coupling of biomolecules or ligands via covalent or non-covalent bonds. Suitable as functional groups are the hydroxyl groups of the polyvinyl alcohol matrix, but also groups introduced via subsequent modification reactions—as mentioned hereinabove. According to a preferred embodiment, the functional groups are bound to the polyvinyl alcohol via spacer molecules.

Suitable as biomolecules or ligands capable of being bound covalently or non-covalently to the magnetizable microparticles are, in particular, antibodies, avidin, biotin, protein A, protein G, lectins, oligosaccharides, oligonucleotides, enzymes, enzyme inhibitors, enzyme substrates, receptor proteins, albumin, gelatine, glutathione, amino acids, peptides, hormones and/or neurotransmitters. Furthermore, any other biomolecules or ligands used according to the state of the art in affinity chromatography or for diagnostic purposes are basically suitable as well.

Owing to their high content (at least 50 percent by weight) of magnetizable nanoparticulate material, preferably magnetite, and owing to their narrow particle size distribution in the range of 0.5 to 3 µm, the spherical, magnetizable polyvinyl alcohol microparticles are particularly suitable for use in automated separation methods, especially for automated nucleic acid purification. Their narrow size distribution facilitates complete separation of the magnetizable microparticles, especially in automated nucleic acid purification.

Furthermore, with the spherical, magnetizable polyvinyl alcohol microparticles of the invention, which may contain more than 50 percent by weight and up to 90 percent by weight of magnetizable material, it is possible to achieve very good magnetic separation properties (that is, rapid, complete and reproducible separation at high yields) despite the reduced or small particle size. As a result, the microparticles according to the invention are especially suited for the treatment of larger sample volumes (e.g. isolation of genomic DNA from 10 ml of whole blood).

In addition, the polyvinyl alcohol microparticles of the invention are also excellently suited for treating very small sample volumes (e.g. 10 µl) since owing to the small particle diameter and the associated large active total surface area, a small mass of particles is sufficient to purify a respective sample.

The polyvinyl alcohol microparticles of the invention can be used, for example, to isolate, purify or enrich cells, nucleic acids, peptides, proteins, toxins, viruses, bacteria, antibodies, enzymes, antigens or receptors. Preferred application areas relate to diagnostic or forensic detection methods in immunoassays, DNA sequencing, PCR product purification, cell fractionation, protein isolation, affinity purification, immunoprecipitation, tissue typing, oligonucleotide synthesis or peptide synthesis.

With the invention, magnetizable microparticles with improved separation properties are provided which are particularly suited for automated separation methods. In addition, by means of the method of production according to the invention, it is possible to produce these particles on a large scale and at a high batch consistency.

EXAMPLES

Example 1: Preparation of a Magnetite Colloid Suspension

Magnetite colloid: The nanocrystalline magnetite is prepared as described above, using known methods. Then, the suspension is washed until salt-free, by repeated centrifuging at 3000×g, for five minutes at a time, and re-suspending in demineralized water until the conductance value of the suspension is less than 500 µS/cm. The magnetite prepared according to the invention has a slightly negative, near-neutral zeta potential (in the range of about −4.5 to −0.5 mV).

180 g of the magnetite thus obtained are suspended in demineralized water and treated for 2 hours in an in-line ultrasonic method (flow method) at a power of at least 1000 W (Dr. Hielscher Sonopuls 2000 W; Hielscher Ultrasonics GmbH, D-14513 Teltow).

Then, 600 ml of a 12.5% polyvinyl alcohol solution (percent by weight) are added and this is sonicated for a further two hours. Subsequently, the suspension is centrifuged at 2000×g, for 10 minutes. A PVA-containing magnetite suspension having a size maximum of 100 nm and a magnetite content of 2.8%, and 1.4% PVA is obtained. The particle size is determined by PCS (Beckman Coulter Delsa™ Nano C).

Example 2: Preparation of Magnetizable Polyvinyl Alcohol Microparticles 5000 ml of the magnetite colloid according to Example 1 are thoroughly mixed with 660 ml HCl (2.5 M). This suspension is added to 60 L of a commercial vegetable oil, which contains 1.5 percent by volume of TWEEN®, 0.5 percent by volume of sorbitan sesquioleate, 2.5 percent by volume Dehymuls® HRE and 0.75 percent by volume of Hypermer® after the organic phase has been heated to 60° C.

Subsequently, stirring is performed for 10 minutes, using a dispersion mixer (Ystral Dispermix), at 60° C. and at a stirring speed of 3500 r/min. Following addition of 550 ml of a 12.5% (in water) glutaraldehyde solution, stirring is continued for another 35 min (Ystral Dispermix, 3500 r/min).

The particles are magnetically separated from the suspension and repeatedly washed with water (no organic solvents). 250 g of magnetite particles of a size of 1-3 µm and having a magnetite content of 55 percent by weight are obtained. The polydispersity index (PDI) is between 0.1 and 0.25. The particle size and the PDI were determined by PCS (Beckman Coulter Delsa™ Nano C).

Example 3: Determination of Zeta Potential

The inventive magnetizable microparticles are characterized, inter alia, in that in biochemical detection methods (particularly in PCR) they cause fewer non-specific bonds, less carry-over of interfering components, etc., than is the case with particles described in the state of the art. It is assumed that this advantageous property is brought about according to the invention by an improved encapsulation of the magnetizable material (magnetite), so that less free, that is, non-encapsulated magnetite is exposed on the particle surface.

Since the presence of non-encapsulated magnetite causes a change in the surface properties of the particles, it is to be assumed that this change can be proved by measuring the zeta potential, which is essentially proportional to the number of the surface charges. This hypothesis was tested as follows:

Polyvinyl alcohol microparticles according to the invention were prepared as described in Example 2. For the purpose of comparison, magnetic polyvinyl alcohol particles were prepared in accordance with WO 97/04862 A1, Example 2. In both cases, the particle size was in the range of 1-3 µm. Subsequently, the zeta potential was measured with samples from several particle batches. The results are shown in Table 1.

TABLE 1

| Batch No. | Zeta potential [mV] |
|---|---|
| Magnetic particles according to WO 97/04862 | |
| 1 | MP121 | −29.41 |
| 2 | MP121 | −30.91 |
| 3 | C238 | −30.38 |
| 4 | C257 | −27.33 |
| 5 | C271 | −26.83 |
| 6 | C283 | −28.74 |
| Ø | | −28.93 |
| Magnetic particles according to the invention | |
| 1 | C348 | −39.59 |
| 2 | C349 | −39.36 |
| 3 | C350 | −39.38 |
| 4 | C351 | −40.12 |
| 5 | C352 | −39.75 |
| Ø | | −39.64 |

The particles prepared according to the methods of the invention exhibit an average zeta potential of about −40 mV, which, compared to the particles prepared in accordance with WO 97/04862, is increased by 30% (relative to the absolute value).

This finding confirms the assumption that in the particles according to the invention the proportion of free magnetite was reduced. The smaller the proportion of free magnetite in the total surface area, and the higher the proportion of the total surface area that is covered with polyvinyl alcohol, the greater is the number of potentially oxidizable functional groups (and thereby potential charge carriers) present on the surface. This manifests itself in a corresponding change of the zeta potential, as shown in Table 1. Since the particle diameter, and hence the total surface area of the particles, always remained constant (1-3 µm), it is to be assumed that the change of zeta potential observed is caused by the reduction of the proportion of free magnetite in the case of the particles according to the invention.

This assumption is corroborated by additional experiments, wherein it could be shown that the zeta potential of the magnetic polymer particles can be lowered again (relative to the absolute value) by incubating the particles with nanocrystalline magnetite. The magnetite binds to the particle surface by van der Waals interactions, and thereby covers a part of the particle surface, so that the charges lying underneath are screened off and thereby become inaccessible. As can be expected, this results in a lowering of the zeta potential (relative to the absolute value), as shown in Table 2.

TABLE 2

|   | Batch No. | Zeta potential [mV] |
|---|-----------|---------------------|
| 1 | C348      | −39.59              |
| 2 | C348 + M  | −32.28              |
| 3 | C349      | −39.36              |
| 4 | C349 + M  | −34.1               |
| 5 | C350      | −39.38              |
| 6 | C350 + M  | −33.13              |
| 7 | C351      | −40.12              |
| 8 | C351 + M  | −33.14              |
| 9 | C352      | −39.75              |
| 10| C352 + M  | −32.98              |

The particles used for the zeta potential measurements shown in Table 2 were particles prepared according to the method of the invention (as in Table 1 and Example 2). The indication "+M" means that the respective samples were incubated with free magnetite.

Due to the more highly negative zeta potential, the magnetizable polyvinyl alcohol particles according to the invention have a lower tendency to form agglomerates, and thus for agglutination, than is the case with the pre-known polyvinyl alcohol particles (WO 97/04862 A1).

Example 4: Behavior of the Magnetizable Polyvinyl Alcohol Microparticles According to the Invention when Used in PCR The extent of the inhibitory influence on PCR of the presence of magnetizable polyvinyl alcohol microparticles in PCR samples was examined. To this end, microparticles according to the invention (see Examples 2 and 3) were compared with conventional particles (WO 97/04862 A1; see Example 3).

The template DNA used in the PCR was obtained by spiking human plasma with a defined phage titre of the bacteriophage Phi X 174, and extracting therefrom the nucleic acids. Then the nucleic acids were amplified by real time PCR. To investigate any inhibitory effects of the magnetizable polymer particles, the magnetizable polyvinyl alcohol microparticles to be examined were added to the amplification reactions, adding 25 µg, 50 µg or 100 µg of particles per reaction batch at a time (see Tables 3 and 4).

In the following Tables 3 and 4 are listed the Ct values determined by real time PCR. The Ct value indicates the number of cycles needed until the fluorescence signal crosses the threshold. In the case of the positive control (PCR reaction without addition of magnetizable polymer particles), the Ct value was 25.00.

TABLE 3

Magnetizable particles according to the invention, Ct values (real time PCR)

|        | 1     | 2     | 3     | 4     | 5     | Ø     |
|--------|-------|-------|-------|-------|-------|-------|
| 25 µg  | 25.00 | 25.00 | 24.72 | 25.00 | 24.69 | 24.88 |
| 50 µg  | 25.00 | 25.02 | 25.07 | 25.14 | 25.10 | 25.07 |
| 100 µg | 25.09 | 25.16 | 25.29 | 25.06 | 25.09 | 25.14 |

The data indicated in columns 1 to 5 of Table 3 relate to different batches of the particles according to the invention.

As can be seen from Table 3, the Ct value remains unchanged, namely at 25. This means that the amplification of the nucleic acids is not inhibited by the particles present in the reaction.

TABLE 4

Magnetizable particles according to the state of the art (WO 97/04862 A1), Ct values (real time PCR)

|        | 1     | 2     | 3     | 4     | 5     | Ø     |
|--------|-------|-------|-------|-------|-------|-------|
| 25 µg  | 26.29 | 26.24 | 26.14 | 26.24 | 26.2  | 26.22 |
| 50 µg  | 26.74 | 26.68 | 26.7  | 26.69 | 26.57 | 26.68 |
| 100 µg | 28    | 28.2  | 28.16 | 28.24 | 28    | 28.12 |

The data shown in columns 1 to 5 of Table 4 relate to different batches of the particles prepared according to WO 97/04862 A1.

In contrast to Table 3 (particles according to the invention), adding the pre-known particles to the PCR resulted in increased Ct values, as a function of the added amount of particles (25/50/100 µg). Addition of 100 µg caused an increase of the Ct value to 28. The increase of the Ct value means a delay in the generation of the fluorescence signals, meaning a delayed amplification of the DNA. Hence, this delay indicates the inhibitory influence of the conventional magnetic particles (WO 97/04862 A1), in contrast to the particles according to the invention, which do not exhibit such an inhibitory effect (Table 3).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

We claim:

1. A method for the production of spherical, magnetizable polyvinyl alcohol microparticles having a particle size distribution in the range of 0.5 to 3 µm, the method comprising steps of:
   dispersing a nanoparticulate, magnetizable material in an aqueous phase which contains polyvinyl alcohol in dissolved form;
   adding the aqueous phase to an organic phase which is immiscible with said aqueous phase and contains at least one emulsifier, and producing an emulsion by stirring at a temperature of 40° C. or higher;
   adding at least one water-soluble crosslinking agent suitable for crosslinking polyvinyl alcohol, while stirring is continued.

2. The method according to claim 1, wherein the magnetizable material is magnetite.

3. The method according to claim 1, wherein the nanoparticulate magnetizable material comprises magnetizable nanoparticles of a particle size in the range of 5 to 250 nm.

4. The method according to claim 1, wherein the nanoparticulate magnetizable material is nanocrystalline magnetite.

5. The method according to claim 1, wherein prior to adding the aqueous phase to the organic phase, said aqueous phase undergoes a treatment by which particles of a size of greater than 250 nm are removed.

6. The method according to claim 1, wherein the concentration of polyvinyl alcohol in the aqueous phase does not exceed 2.0 percent by weight.

7. The method according to claim 1, wherein the concentration of the nanoparticulate magnetizable material in the aqueous phase is 0.5 to 7.5 percent by weight.

8. The method according to claim 1, wherein the organic phase comprises one or more substances selected from the group consisting of vegetable oils, synthetic oils, mineral oils, silicone oils and paraffin oils.

9. The method according to claim 1, wherein the proportion of emulsifier contained in the organic phase is 0.1 to 10 percent by weight.

10. The method according to claim 1, wherein the crosslinking agent is selected from the group consisting of bifunctional aldehydes, acid chlorides, and divinyl sulfone.

11. The method according to claim 1, wherein the crosslinking agent is added in liquid form, and the proportion of said crosslinking agent is to 0.1 to 10 percent by volume, relative to the aqueous phase.

12. The method according to claim 1, wherein bifunctional aldehydes are used as the crosslinking agent, and the crosslinking reaction is performed with addition of an acid, with 1N to 3N hydrochloric acid at a volume percent of up to 10%, relative to the aqueous phase.

13. The method according to claim 1, wherein the emulsion is produced by stirring at a temperature of at least 50° C.

14. The method according to claim 1, wherein the emulsion is produced by using a dispersion mixer which operates according to the rotor-stator principle.

15. The method according to claim 1, wherein the nanoparticulate, magnetizable material is of a particle size not exceeding 250 nm, the concentration of polyvinyl alcohol in the aqueous phase does not exceed 2.0 percent by weight, the crosslinking agent is at least one bifunctional aldehyde, and the crosslinking reaction is performed with addition of an acid, with 1N to 3N hydrochloric acid at a volume percent of up to 10%, relative to the aqueous phase.

16. The method according to claim 1, wherein the concentration of polyvinyl alcohol in the aqueous phase does not exceed 2.0 percent by weight, the emulsion is produced using a dispersion mixer which operates according to the rotor-stator principle at a rotor speed in the range of 500 to 4000 revolutions/min, and the volume of the emulsion is 10 L or more.

17. The method according to claim 1, wherein the concentration of polyvinyl alcohol in the aqueous phase does not exceed 2.0 percent by weight, the emulsion is produced using a dispersion mixer which operates according to the rotor-stator principle at a rotor speed in the range of 500 to 4000 revolutions/min, the volume of the emulsion is 10 L or more, the crosslinking agent is at least one bifunctional aldehyde, and the crosslinking reaction is performed with addition of an acid, with 1N to 3N hydrochloric acid at a volume percent of up to 10%, relative to the aqueous phase.

18. The method according to claim 1, wherein the nanoparticulate magnetizable material used is subjected to a treatment method comprising steps of:
   suspending magnetizable nanoparticles in deionized water having a conductance of less than 100 µS/cm; and
   treating the aqueous nanoparticle suspension with an ultrasound homogenizer.

19. The method according to claim 18, wherein the treatment method further comprises a centrifugation step in which particles of a size greater than 250 nm are separated from the nanoparticle suspension.

20. A spherical, magnetizable polyvinyl alcohol microparticle produced by the method according to claim 1, having a particle size distribution in the range of 0.5 to 3 µm, and containing nanoparticulate magnetizable material at a percentage of at least 50 percent by weight.

21. The spherical, magnetizable polyvinyl alcohol microparticle according to claim 20, having a particle size distribution in the range of 1.25 to 2.25 µm.

22. The spherical, magnetizable polyvinyl alcohol microparticle according to claim 20, wherein the zeta potential of the microparticles is less than or equal to −35 mV.

23. The spherical, magnetizable polyvinyl alcohol microparticle according to claim 20, wherein when used in real time quantitative PCR, the microparticle causes an increase of the Ct value of 2% or less.

24. The spherical, magnetizable polyvinyl alcohol microparticle according to claim 20, wherein the microparticle contains nanoparticulate magnetizable material at a percentage of at least 60 percent by weight.

25. The spherical, magnetizable polyvinyl alcohol microparticle according to claim 20, further comprising functional groups which enable the coupling of biomolecules or ligands via covalent or non-covalent bonds.

26. The spherical, magnetizable polyvinyl alcohol microparticles according to claim 20, wherein one or more biomolecules or ligands are covalently or non-covalently bound to the particles.

27. The spherical, magnetizable polyvinyl alcohol microparticles according to claim 26, wherein the one or more biomolecules or ligands are selected from the group consisting of antibodies, avidin, biotin, protein A, protein G, lectins, oligosaccharides, oligonucleotides, enzymes, enzyme inhibitors, enzyme substrates, receptor proteins, albumin, gelatine, glutathione, amino acids, peptides, hormones and neurotransmitters.

* * * * *